(12) United States Patent
Liu

(10) Patent No.: US 6,520,025 B2
(45) Date of Patent: *Feb. 18, 2003

(54) POINTING BAR FATIGUE TESTING APPARATUS

(75) Inventor: Chia-Hung Liu, Taipei (TW)

(73) Assignee: Darfon Electronics Corp., Taoyuan (TW)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/559,587

(22) Filed: Apr. 28, 2000

(65) Prior Publication Data

US 2002/0174726 A1 Nov. 28, 2002

(30) Foreign Application Priority Data

May 4, 1999 (TW) .......................... 88206988 U

(51) Int. Cl.[7] ................................. G01N 3/32
(52) U.S. Cl. .............. 73/808; 73/812; 73/849
(58) Field of Search .................. 73/808, 810, 811, 73/806, 794, 812, 813, 814, 815, 841, 849, 854; 367/87; 409/231

(56) References Cited

U.S. PATENT DOCUMENTS 5,544,530 A * 8/1996 Rudisill et al. ............... 73/810
5,913,246 A * 6/1999 Simonelli et al. ............. 73/808

* cited by examiner

*Primary Examiner*—Max Noori
(74) *Attorney, Agent, or Firm*—Troxell Law Office PLLC

(57) ABSTRACT

A pointing bar fatigue testing apparatus for fatigue testing upon various shapes of pointing bars includes a power source, a force feeding device and a pointing bar seat. The power source includes a motor and a rotation spindle extending upwardly. The force feeding device includes a flat board engaged with and rotationally driven by the spindle, a slide bar having a center bore and two ends engageable with two border flanges located at two ends of the flat board and a spring engaged with one end of the slide bar for exerting force on the center bore. The pointing bar seat is located above the force feeding device. When performing pointing bar fatigue testing, the pointing bar has one end fixed on the pointing bar seat and another end engaged with the center bore to receive a spring force through the center bore while the force feeding device is rotated by the power source.

10 Claims, 6 Drawing Sheets

POINTING BAR FATIGUE TESTING APPARATUS

FIELD OF THE INVENTION

This invention relates to a testing apparatus and more particularly to a pointing bar fatigue testing apparatus for fatigue destruction test upon pointing bars used in input devices.

BACKGROUND OF THE INVENTION

The pointing bar input means are widely used in various types of input devices such as control panels, keyboards, remote control devices and the like. The pointing bar input means can also be seen in some other type of the electronic devices such as mouses, joy sticks, touch pads, track balls, pointing sticks and the like. The basic design of pointing bar structure is to produce analog signals resulting from strain caused by a force applying on the pointing bar at a selected direction. The analog signals are output for further computer use. For instance, a pointing bar may be installed between any two adjacent keys in a keyboard of a notebook computer, and a corresponding strain can be produced by a force applied to the top of the pointing bar.

By means of design and arrangement, the strain incurred in the pointing bar may be converted into respective output signals that may be used as movement reference of the computer cursor.

Regarding the production of the pointing bars, especially the strut-type bars, fatigue strength is an important indicator of the production quality. Thus, sampling fatigue strength test is one of the test items during the manufacturing process of the pointing bars.

Generally, it is known that when material is subjected to a force or stress greater than its tensile strength, the material may result in instant fracture. On the other hand, if the stress is smaller than the tensile strength, repeating stress can also lead to a crack in the material, which may grow and result in final fracture after a period of time. As well known in the art, 90% of the material fracture are amounted to fatigue, either static or dynamic. In the case that the repeating stress is dynamic in nature, the resulted fracture is called a dynamic fatigue fracture. In the case that the repeating stress is static in nature, the fracture is called a static fatigue Because the pointing bar is short and brittle (usually made of ceramics), a conventional fatigue testing apparatus cannot be applied. Thus, special testing apparatus are usually needed to carry out the testing of the pointing bar. In U.S. Pat. No. 5,544,530, Rudisill et al disclosed one of the special apparatus for fatigue testing of the pointing bars.

FIG. 1 illustrates a schematic view of the testing apparatus taught by Rudisill et al. As shown, the apparatus has a motor with which a spindle 13 can rotate. The spindle 13 further contacts forcedly and eccentrically with an elastic arm 15 via a round disk 17 at one end thereof so that the elastic arm 17 can be slightly bent in the middle portion. The bending force applied to the disk 17 can thus be transmitted to pointing bar 11 axially engaged with the center of the disk 17. When the motor is actuated, the rotating spindle 13 will drive the elastic arm 15 running around the disk 17 and consequently applying moving bending stress upon the pointing bar 11 to mimic radial and repeating forces upon the pointing bar.

However the prior art set forth above has the following shortcomings:

1. The elastic arm makes the motor rotation not even, nor stable. It can only be used for low speed testing. Therefore, the test scope and result are limited and time-consumed.
2. It does not take into account the centrifugal force resulting from the rotating elastic arm. The force assigned to the pointing bar is not equal to the actual force received by the pointing bar, and thus the testing result cannot tell a true story.
3. As the elastic arm is horizontally positioned, the effect of gravitational force should be included. Upon including the gravitational force, the resultant force upon the pointing bar is the greatest when the elastic arm moves to the highest portion of the disk 17 and is the lowest when it moves to the lowest portion of the disk 17.

Hence, there is still a need for developing a pointing bar fatigue testing apparatus that can reduce the effect of the gravitational force and the centrifugal force and may perform the test speedily without sacrificing the system stability.

SUMMARY OF THE INVENTION

In view of aforesaid disadvantages, this innovation aims at providing a pointing bar fatigue testing apparatus that has a horizontal rotating disk for holding the pointing bar vertically to free the effect of gravitational force, so that the problems resulting from not evenly and not accurately applying force may be resolved.

It is an object of this invention to provide a pointing bar fatigue testing apparatus that is characterized on simple structured, evenly force applying, no gravitational force impact, and accurate performance.

The pointing bar fatigue testing apparatus of this invention may perform fatigue test for different shapes of pointing bar. It mainly includes a power source, a force feeding means and an pointing bar seat. The power source may be a motor having an extending spindle.

The force feeding means has a flat board, a slide bar and a motor spindle. The flat board has two spaced border flanges which have respective round openings therein for holding the slide bar. The slide bar has a bore in the middle. There is a spring engaging with one end of the slide bar and exerting spring force on the bore.

The pointing bar seat is preferably a modular member located above the force feeding means.

When in use, one end of the pointing bar is fixed to the pointing bar seat and another end engages with the bore in the slide bar. When the power source rotates the force feeding means, the spring exerts force on the pointing bar located through the bore for performing fatigue testing upon the pointing bar.

In an embodiment of this invention, there is a sensor means located below the power source for sensing the rotation speed of the power source disk plate. A controller may be included to wire with the sensor means for indicating and controlling the power source rotation speed.

In another embodiment of this invention, the power source may include a reducer which may be a gear set, a friction wheel set, a belt pulley set and the like. The gear set may be a combination of a large gear and a small gear for reducing rotation speed from the power source to the force feeding means.

In yet another embodiment of this invention, the slide bar may include a bearing located in the middle thereof. An inner ring of the bearing can form a force transmission point to the pointing bar.

In a still another embodiment, the force feeding means may include at least one side wall for supporting at least one side of the force feeding means. It is preferably to have two side walls for supporting two sides of the force feeding means. The side wall may slidably engage with the force feeding means to adjust the position of the force feeding means.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

In the following description and figures, similar components will be marked by respective identical numerals.

Figure 1:
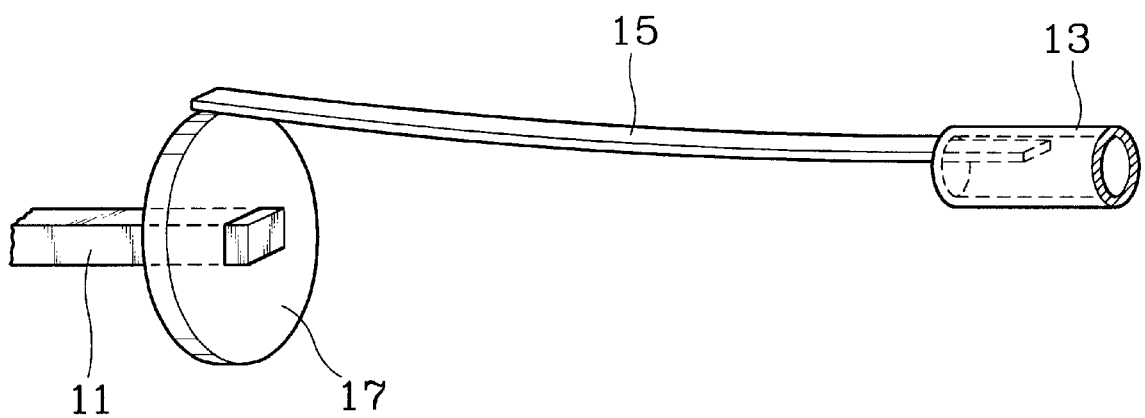
FIG. 1 is a fragmentary perspective view of a conventional pointing bar fatigue testing apparatus.
Figure 2:
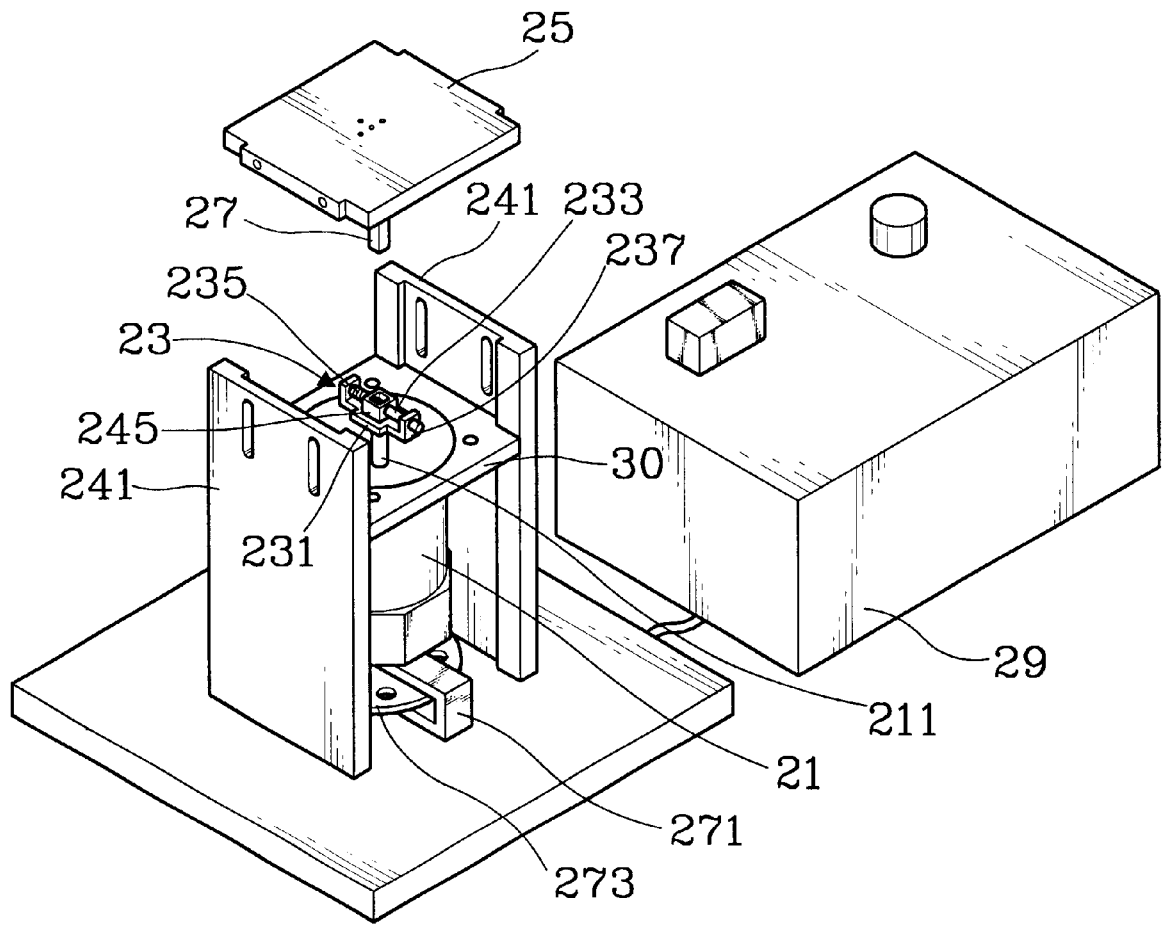
FIG. 2 is a perspective view of an embodiment of this invention.

Referring to FIG. 2, the pointing bar fatigue testing apparatus according to this invention may be used for a fatigue test on different shapes of pointing bar. The apparatus mainly constitutes a body, a sensor means for measuring rotation speed and a controller 29.

The body includes a power source 21, a force feeding means 23 and an pointing bar seat 25. The power source 21 is wired to the sensor means and the controller 29. The sensor means may include a sensor 271 and a disk plate 273. When the power source 21 rotates, it drives the disk plate 273 to rotate. The sensor 271 may sense and measure the rotation speed of the disk plate 273. The rotation speed of the power source 21 thus may be transmitted to the controller 29 through the sensor means. The controller 29 may display and control the rotation speed.

The power source 21 may be a motor which has a spindle 211 extended upward to engage with the force feeding means 23. Thus the power source 21 may drive the force feeding means 23 to rotate.

The pointing bar seat 25 may be a modular member for mating different shapes of pointing bars. It is located above the force feeding means 23. The pointing bar 27 has one end engaged with the pointing bar seat 25 and another end engaged with the force feeding means.

The force feeding means 23 has a flat board 231, a slide bar 233 and a spring 235. The slide bar 233 has a hollow frame 245 in the middle portion which further has a bore 239 formed therein. The flat board 23 has two spaced border flanges 237 at two sides, and each of the border flanges 237 has a round hole formed therein for holding one end of the slide bar 233. The slide bar 233 is slidable through the round holes horizontally and axially. It is noted that, instead of the slide bar 233 and the border flanges 237, other means such as a slide trough (couples with sliding blocks at two ends of the slide bar 233) or a guide rail (couples with slide seats formed at two ends of the slide bar 233) may also be used with equal effect.

Between the force feeding means 23 and the power source 21, a partition board 30 may be provided. The partition board 30 is supported at two lateral sides thereof respectively by a side wall 241 and forms an indented space between the side walls 241 above the partition board 30. The pointing bar seat 25 may be slideably held in the indented space.

Figure 3:
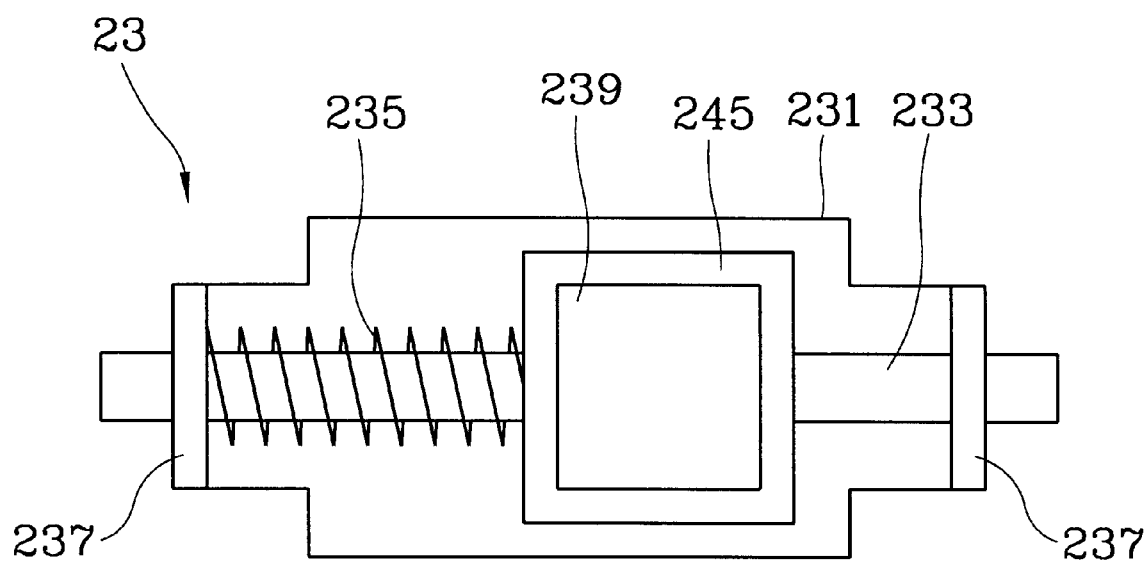
FIG. 3 is a top view of an embodiment of a force feeding means of this invention.

Referring to FIG. 3, the flat board 231 may be rotated by the power source. Hence the rotation of the power source will drive the entire force feeding means to rotate.

The spring 235 is located at one end of the slide bar 233 between the border flange 237 and the frame 245, and it will also push the frame 245 and the bore 239 toward the border flange 237 at another end.

Figure 4:
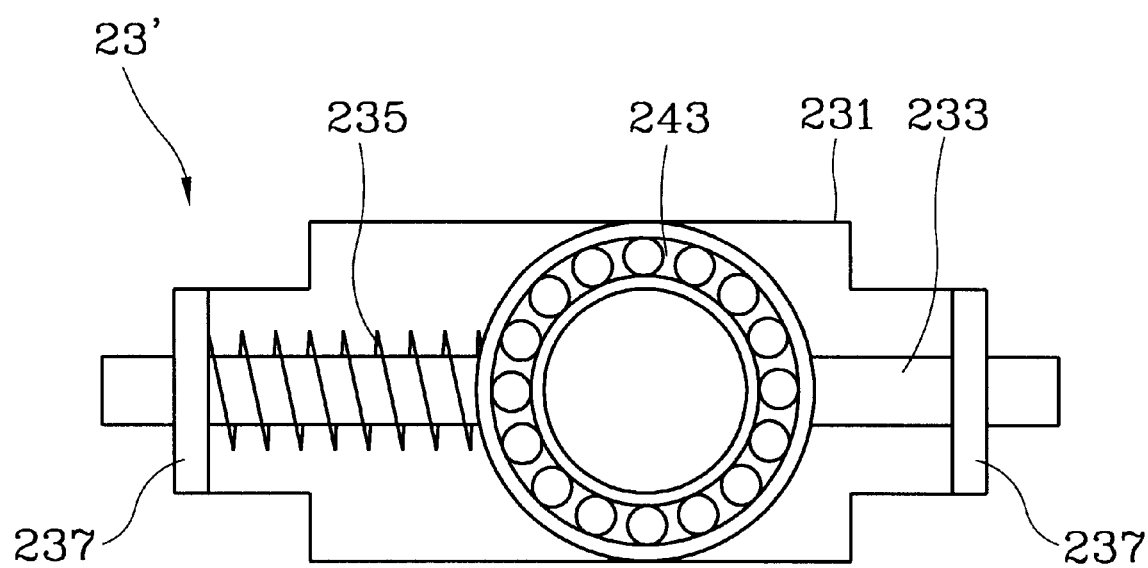
FIG. 4 is a top view of another embodiment of a force feeding means of this invention.

FIG. 4 shows another embodiment of the force feeding means 23 which is largely constructed like the one shown in FIG. 3. However, in this embodiment, a bearing 243 is used to replace the frame 245 of the previous embodiment. The inside diameter of the bearing 243 is larger than the diagonal length of the pointing bar.

Figure 5:
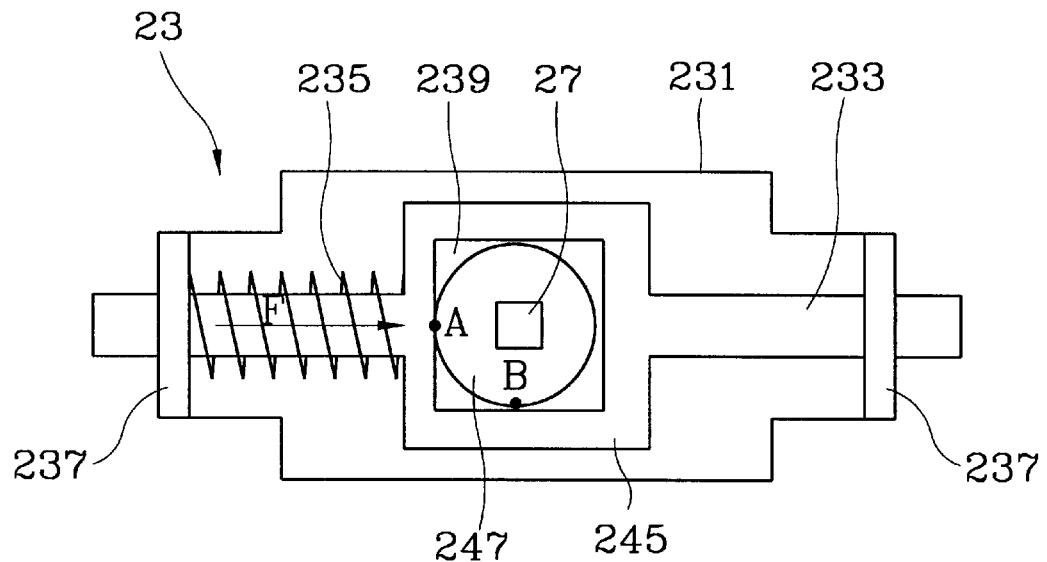
FIG. 5A is a top view of the force feeding mean shown in FIG. 3 in use, at one rotating position.
FIG. 5B is a top view of the force feeding means shown in FIG. 3 in use, at another rotating position.
Figure 5:
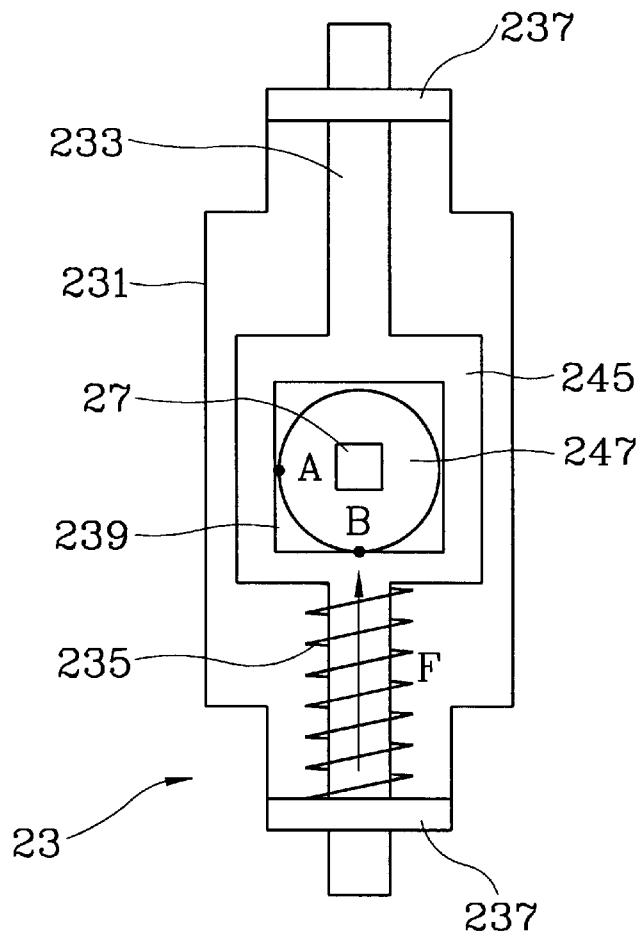

FIGS. 5A and 5B show an application of the embodiment depicted in FIG. 3. The pointing bar 27 to be tested has one end held in the pointing bar seat and another end held in an opening formed in a disk 247 which is held in the bore 239. The disk 247 is preferably circular. The opening is mating with the cross-section of the pointing bar 27 for providing positive engagement between the pointing bar 27 and the disk 247.

The pointing bar 27 is preferably coaxial aligned with the spindle 211 at the same center line. Then the spring 235 will have its spring force F applying on the pointing bar 27 at the point A through the frame 245, and produce a bending stress in the pointing bar 27.

When the power source 21 drives the force feeding means 23 to rotate, the slide bar 233 and the frame 245 can also rotate as shown in FIG. 5B. However, the disk 247 and the pointing bar 27 remain stationary because being held by the pointing bar seat 25 and the side wall 241. The pointing bar 27 thus receives a spring force F at different location and direction such as point B shown in FIG. 5B, when the feeding means 23 rotates 90 degree counterclockwise or 270 degree clockwise from point A. Since the pointing bar 27 is held vertically, the spring force F is evenly applying to the pointing bar 27 in the rotational direction. Hence, the fatigue test on effect by the centrifugal and gravitational forces.

Figure 6:
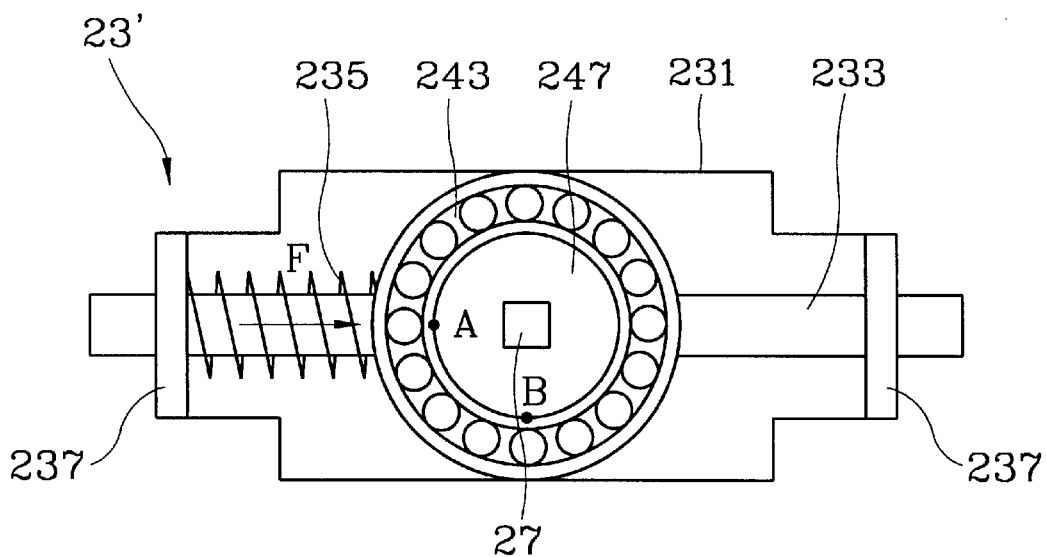
FIG. 6A is a top view of the force feeding means shown in FIG. 4 in use, at one rotating position.
FIG. 6B is a top view of the force feeding means shown in FIG. 4 in use, at another rotating position.
Figure 6:
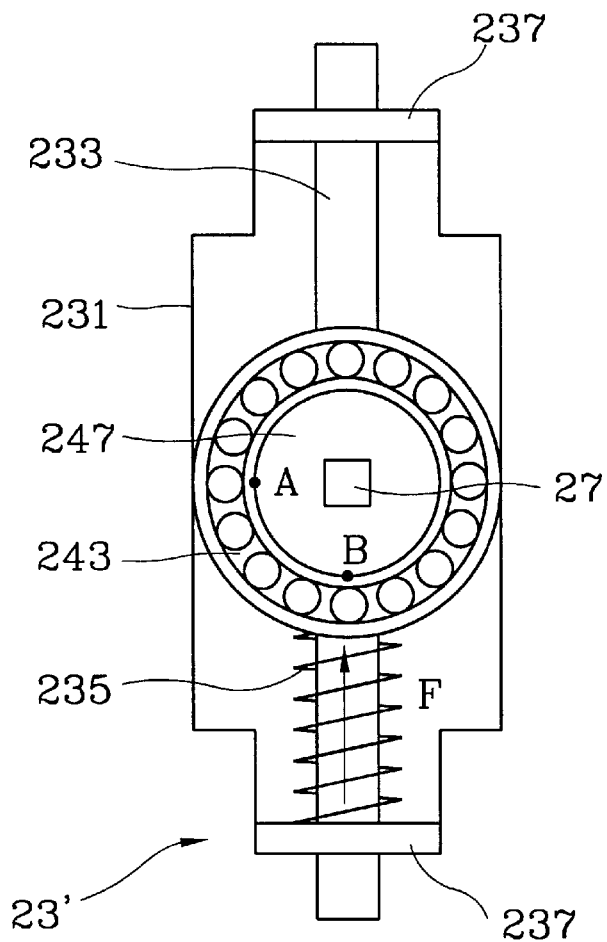

FIGS. 6A and 6B show the same embodiment depicted in FIG. 4 in use. They are largely like the ones, shown in FIGS. 5A and 5B except that the bearing 243 replaces the frame 245, and the inner ring of the bearing 245 making contact with the disk 247 rather than the bore 239. The operation principle of this embodiment is eventually the same as the previous embodiment. However, the inner ring of the bearing 243 may offer lower friction than the bore 239 when the force feeding means 23 rotates around the disk 247.

This invention basically uses the flat board 231 to provide a horizontal rotation base for the slide bar 233 to slide horizontally between the border flanges 237 so that the spring force may apply to the pointing bar around a circular perimeter of the disk 247. The structure of the border flanges 237 and the slide bar 233 may be replaced by other similar means equally well such as a slide trough (couples with slide blocks at two ends to replace the slide bar 233), a guide rail (couples with slide seat at two ends to replace the slide bar 233) and the like.

Figure 7:
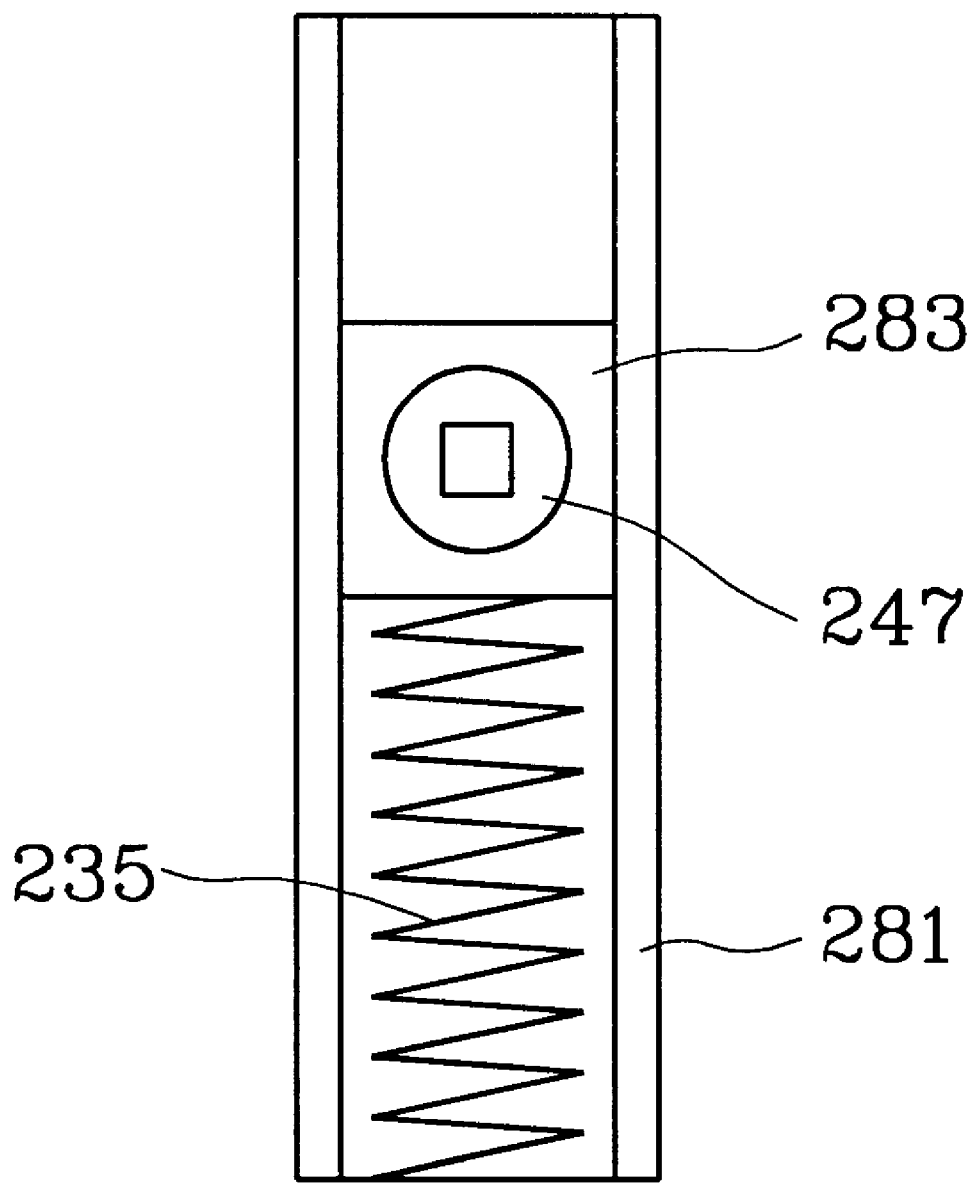
FIG. 7 is a top view of another embodiment force feeding means of this invention.

FIG. 7 shows another embodiment of the force feeding means 23. It has a chute 281 located on and extended from the flat board containing a slide block 283 therein. The slide block 283 has a bore to engage with the disk 247. At one end of the chute 281, there is a spring 235 making contact with one side of the slide block 283 for exerting spring force upon the pointing bar held in the disk 247. Another end of the chute 281 is fixed on the force feeding means. Therefore, when the force feeding means rotates, the pointing bar will receive bending stress evenly from all directions of the rotation. The spring 235 may also be substituted by other elastic means known in the art, such as rubber, a coil spring and the like.

It may thus be seen that the objects of the present invention set forth herein, as well as those made apparent from the foregoing description, are efficiently attained. While the preferred embodiments of the invention have been set forth for purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A test assembly for mechanically testing a pointing bar through all directions of lateral deflection, comprising:
    a) a power source having a rotatable, vertically oriented spindle;
    b) a force feeding device rotated by rotation of the spindle, the force feeding device including:
        i) a flat board rotated by rotation of the spindle;
        ii) a slide bar mounted on the flat board;
        iii) a hollow frame on the slide bar whereby the hollow frame being linearly movable relative to the flat board; and
        iv) a biasing device acting on the hollow frame and exerting a biasing force thereon; and,
    c) a pointing bar seat configured for holding and positioning the pointing bar such that the pointing bar and the spindle are coaxial, a first end of the pointing bar being rigidly connected to the pointing bar seat and a second end of the pointing bar mechanically coupled in the hollow frame, whereby linear movement of the hollow frame applies a lateral force in all directions around a circumference of the second end of the pointing bar as the spindle rotates.

2. The test assembly of claim 1 further comprising a sensor located below the power source for sensing a rotation speed of the spindle.

3. The test assembly of claim 1 wherein the sensor includes a controller connected to the sensor for indicating and controlling the power source rotation speed.

4. The test assembly of claim 1 wherein the hollow frame comprises a bearing.

5. The test assembly of claim 1 wherein the flat board includes two spaced apart flanges supporting the slide bar.

6. The test assembly of claim 1 wherein the power source is a motor.

7. The test assembly of claim 6 wherein the motor is a constant speed motor.

8. The test assembly of claim 1 wherein the pointing bar seat is a modular member.

9. The test assembly of claim 1 wherein the flat board has a chute and wherein the hollow frame is linearly movable along the chute.

10. The test assembly of claim 1 wherein the biasing device is a spring.

* * * * *